(12) United States Patent
Standley

(10) Patent No.: US 8,735,261 B2
(45) Date of Patent: May 27, 2014

(54) METHOD AND SYSTEM FOR STRIPPING THE EDGE OF A SEMICONDUCTOR WAFER

(75) Inventor: Robert W. Standley, Chesterfield, MO (US)

(73) Assignee: MEMC Electronic Materials, Inc., St. Peters, MO (US)

( * ) Notice: Subject to any disclaimer, the term of this patent is extended or adjusted under 35 U.S.C. 154(b) by 331 days.

(21) Appl. No.: 13/130,160

(22) PCT Filed: Nov. 16, 2009

(86) PCT No.: PCT/US2009/064545
§ 371 (c)(1),
(2), (4) Date: May 25, 2011

(87) PCT Pub. No.: WO2010/059556
PCT Pub. Date: May 27, 2010

(65) Prior Publication Data
US 2011/0223741 A1    Sep. 15, 2011

Related U.S. Application Data

(60) Provisional application No. 61/116,105, filed on Nov. 19, 2008.

(51) Int. Cl.
*H01L 21/762* (2006.01)
*C23F 1/08* (2006.01)
*H01L 21/306* (2006.01)

(52) U.S. Cl.
USPC 438/458; 156/345.23; 438/747; 257/E21.219; 257/E21.567

(58) Field of Classification Search
None
See application file for complete search history.

(56) References Cited

U.S. PATENT DOCUMENTS

| | | |
|---|---|---|
| 3,964,957 A | 6/1976 | Walsh |
| 4,113,543 A | 9/1978 | Salles et al. |
| 4,251,317 A | 2/1981 | Foote |
| 4,388,140 A | 6/1983 | Nakazato et al. |
| 4,588,473 A | 5/1986 | Hisatomi et al. |
| 4,849,701 A | 7/1989 | Saatkamp et al. |

(Continued)

FOREIGN PATENT DOCUMENTS

| | | |
|---|---|---|
| EP | 529888 A1 | 3/1993 |
| EP | 744082 A1 | 11/1996 |

(Continued)

OTHER PUBLICATIONS

Examination Report issued in related European Patent Application No. 09 761 085.1-1551 dated Feb. 28, 2013, 9 pgs.

(Continued)

*Primary Examiner* — Seahvosh Nikmanesh
(74) *Attorney, Agent, or Firm* — Armstrong Teasdale LLP

(57) ABSTRACT

A method and a system are described herein for applying etchant to edges of a plurality of wafers. The system includes a sump configured for holding etchant, a roller having an outer surface in fluid communication with the sump and configured to have etchant thereon, a wafer cassette configured to retain wafers positioned therein so that edges of the wafers are in contact with the roller. The cassette permits axial rotation of the wafers about an axis. A method of applying etchant to the edge of the wafer includes placing the wafer edge in contact with the roller and rotating the roller about a longitudinal axis of the roller. At least a portion of the roller contact an etchant contained in a sump during rotation so that etchant is applied to the wafer edge.

15 Claims, 6 Drawing Sheets

(56) References Cited

U.S. PATENT DOCUMENTS

| | | | |
|---|---|---|---|
| 4,971,645 A | 11/1990 | Licus | |
| 5,211,794 A | 5/1993 | Enomoto et al. | |
| 5,233,218 A | 8/1993 | Miura | |
| 5,236,548 A | 8/1993 | Stadler et al. | |
| 5,246,528 A | 9/1993 | Hasegawa et al. | |
| 5,340,437 A | 8/1994 | Erk et al. | |
| 5,425,846 A | 6/1995 | Koze et al. | |
| 5,668,045 A | 9/1997 | Golland et al. | |
| 5,783,097 A | 7/1998 | Lo et al. | |
| 5,834,812 A | 11/1998 | Golland et al. | |
| 5,843,322 A | 12/1998 | Chandler, Jr. | |
| 5,879,577 A | 3/1999 | Weng et al. | |
| 5,933,902 A | 8/1999 | Frey | |
| 5,945,351 A | 8/1999 | Mathuni | |
| 6,046,117 A | 4/2000 | Bauer et al. | |
| 6,110,839 A | 8/2000 | Nakano et al. | |
| 6,117,778 A | 9/2000 | Jones et al. | |
| 6,152,507 A | 11/2000 | Pirker | |
| 6,162,739 A | 12/2000 | Sumnitsch et al. | |
| 6,273,950 B1 | 8/2001 | Kitabatake | |
| 6,294,469 B1 | 9/2001 | Kulkarni et al. | |
| 6,309,981 B1 | 10/2001 | Mayer et al. | |
| 6,328,846 B1 | 12/2001 | Langen et al. | |
| 6,333,275 B1 | 12/2001 | Mayer et al. | |
| 6,368,192 B1 | 4/2002 | Jones et al. | |
| 6,383,060 B2 | 5/2002 | Kawasaki et al. | |
| 6,395,646 B1 | 5/2002 | Liu | |
| 6,482,749 B1 | 11/2002 | Billington et al. | |
| 6,494,221 B1 | 12/2002 | Sellmer et al. | |
| 6,497,784 B1 | 12/2002 | Jones et al. | |
| 6,503,363 B2 | 1/2003 | Nakano et al. | |
| 6,523,553 B1 | 2/2003 | Redeker et al. | |
| 6,586,342 B1 | 7/2003 | Mayer et al. | |
| 6,833,063 B2 | 12/2004 | Basol | |
| 6,881,675 B2 | 4/2005 | Pan et al. | |
| 6,939,807 B2 | 9/2005 | Yun et al. | |
| 7,007,702 B2 | 3/2006 | Langen | |
| 7,029,567 B2 | 4/2006 | Basol | |
| 7,323,421 B2 | 1/2008 | Stinson et al. | |
| 2001/0015170 A1 | 8/2001 | Kitabatake | |
| 2003/0116444 A1 | 6/2003 | Basol | |
| 2003/0141201 A1 | 7/2003 | Basol | |
| 2003/0216046 A1 | 11/2003 | Pan et al. | |
| 2004/0077159 A1 | 4/2004 | Yun et al. | |
| 2004/0084315 A1 | 5/2004 | Mizohata et al. | |
| 2004/0251518 A1 | 12/2004 | Preusse et al. | |
| 2005/0150867 A1 | 7/2005 | Sax | |
| 2006/0026683 A1 | 2/2006 | Lim | |
| 2006/0115986 A1 | 6/2006 | Donohoe et al. | |
| 2006/0137994 A1 | 6/2006 | Basol et al. | |
| 2006/0172538 A1 | 8/2006 | Itzkowitz et al. | |
| 2006/0205217 A1 | 9/2006 | Pan et al. | |
| 2006/0252272 A1 | 11/2006 | Koyata et al. | |
| 2006/0266383 A1 | 11/2006 | Tran et al. | |
| 2007/0161247 A1 | 7/2007 | Koyata et al. | |
| 2009/0242126 A1 | 10/2009 | Erk et al. | |
| 2009/0246444 A1 | 10/2009 | Erk et al. | |
| 2009/0247055 A1 | 10/2009 | Erk et al. | |

FOREIGN PATENT DOCUMENTS

| | | |
|---|---|---|
| EP | 0544131 B1 | 3/1997 |
| EP | 774776 A2 | 5/1997 |
| EP | 1058300 A2 | 6/2000 |
| EP | 1058300 A2 | 12/2000 |
| EP | 924148 B1 | 1/2001 |
| EP | 1456868 A2 | 9/2004 |
| EP | 1662560 A2 | 5/2006 |
| EP | 1855309 A1 | 11/2007 |
| JP | 57141926 A2 | 2/1982 |
| JP | 2015628 A | 1/1990 |
| JP | 5013388 A | 1/1993 |
| JP | 6244167 A | 9/1994 |
| JP | 08274286 A | 10/1996 |
| JP | 10056006 A | 2/1998 |
| JP | 2000082690 A | 3/2000 |
| JP | 2001044147 A | 2/2001 |
| JP | 2001044170 A | 2/2001 |
| JP | 2002043294 A | 2/2002 |
| JP | 2002110626 A | 4/2002 |
| JP | 2002170808 A | 6/2002 |
| JP | 2002334879 A | 11/2002 |
| JP | 2003045845 A | 2/2003 |
| JP | 2004111439 A | 4/2004 |
| JP | 2004149895 A | 5/2004 |
| JP | 2004296810 A | 10/2004 |
| JP | 2005005701 A | 1/2005 |
| WO | 96/17377 A1 | 6/1996 |
| WO | 97/27621 A1 | 7/1997 |
| WO | 03/060963 A2 | 7/2003 |
| WO | 2006/060752 A2 | 6/2006 |
| WO | 2006092886 A1 | 9/2006 |
| WO | 2010098007 A1 | 9/2010 |

OTHER PUBLICATIONS

Office Action dated May 27, 2011 in Co-Owned U.S. Appl. No. 12/415,274.
Co-Owned U.S. Appl. No. 12/415,274, filed Mar. 31, 2009.
Co-Owned U.S. Appl. No. 12/415,551, filed Mar. 31, 2009.
Co-Owned U.S. Appl. No. 12/415,555, filed Mar. 31, 2009.
PCT International Search Report and Written Opinion of the International Searching Authority mailed on Jan. 1, 2010 regarding PCT/US2009/064545 filed on Nov. 15, 2009, 15 pages.
Written Opinion issued in related Singapore Patent Application No. 201103600-1 dated May 25, 2012; 8 pages.
International Search Report and Written Opinion for related Application No. PCT/US2009/038975 dated Jun. 30, 2009.

METHOD AND SYSTEM FOR STRIPPING THE EDGE OF A SEMICONDUCTOR WAFER

BACKGROUND

The embodiments described herein generally relate to the manufacture of silicon wafers, and more particularly to a method for stripping an insulator from the edge of a semiconductor wafer.

Semiconductor wafers are generally prepared from a single crystal ingot (e.g., a silicon ingot) which is trimmed and ground to have one or more flats or notches for proper orientation of the wafer in subsequent procedures. The ingot is then sliced into individual wafers. An individual donor wafer is bonded to a handle wafer to form a bonded wafer pair. Either the donor wafer or the handle wafer or both may have an insulating layer (e.g., an oxide layer) deposited on them prior to bonding. Subsequent processes are performed upon the bonded wafer pair, whereby the majority of the thickness of the donor wafer is removed, leaving a thin layer of silicon atop a thin layer of insulator bonded to the upper surface of the handle wafer (i.e. a silicon-on-insulator or SOI wafer).

The layers transferred from the donor wafer to the handle wafer do not extend to the radial edges of the bonded wafer, and instead terminate between one and five millimeters inward from the edge of the bonded wafer. A narrow annulus of exposed handle wafer (i.e., a terrace region) is left around the periphery of the bonded wafer. If an insulating layer is deposited on the handle wafer prior to bonding, the terrace region will be covered by this insulating layer. Silicon dioxide ("oxide") is a commonly used insulating layer. Other insulating layers may be used if the composition of an etchant used to remove the layers is modified.

During subsequent processes such as a high temperature, gas phase etching in an HCl-containing ambient atmosphere to smooth and thin the top silicon layer surface (i.e., an epi-smoothing process), or an epitaxial silicon deposition to thicken the top silicon layer (i.e., an epi-thickening process) the presence of the insulating layer in this terrace region is generally deleterious. In the case of epi-smoothing, the presence of the insulating layer affects the etch rate of the top silicon layer adjacent to the terrace region, leading to undesirable thickness variations in the top silicon layer near the wafer edge. In the case of epi-thickening, in addition to a disruption of the epi deposition rate adjacent to the terrace, small islands of polysilicon can nucleate and grow on the insulating layer in the terrace region and produce nodule defects that negatively impact subsequent use of the wafer or component produced therefrom. Accordingly, removal of the insulating layer in the narrow annulus dramatically reduces the top silicon layer thickness variation and likelihood of defects being formed in the annulus during subsequent operations.

Previous systems for removing or stripping the oxide from the annulus portion of the bonded wafer only permit a single wafer to be processed at a time in what is commonly referred to as a spin etcher. Spin etchers generally direct an etchant at the terrace region while spinning the bonded wafer. Accordingly, the removal of silicon oxide in a spin etcher is a time-consuming and expensive owing to the cost of operation of the spin etcher. Furthermore, only one wafer can be processed at a time in a spin etcher.

Thus, there remains an unfulfilled need for a wafer edge treatment method that addresses the disadvantages of current edge treatment operations and is suitable for use in wafer processing operations utilizing bonded wafers.

BRIEF SUMMARY

A first aspect is directed to a wafer edge etchant application system for applying etchant to edges wafers. The system comprises a sump configured for holding etchant, a roller having an outer surface in fluid communication with the sump and configured to have etchant thereon, and a wafer cassette configured to retain wafers positioned therein so that edges of the wafers are in contact with the roller and the cassette permitting axial rotation of wafers about an axis. Some of the wafers have a handle oxide in a terrace region and the system is configured to strip the handle oxide from the terrace region to improve layer thickness uniformity adjacent to the terrace region and inhibit nodule growth in the terrace region.

Another aspect is directed to a method of applying etchant to the edge of a wafer. The method comprises placing the wafer edge in contact with a roller and rotating the roller about a longitudinal axis of the roller. At least a portion of the roller contacts an etchant contained in a sump during rotation so that etchant is applied to the wafer edge. The step of placing the wafer edge includes placing the wafer in a wafer cassette. The cassette prevents lateral movement of the wafer while permitting rotation about an axis perpendicular to a planar surface of the wafer, wherein the axis is parallel to a longitudinal axis of the roller. Multiple wafers are placed in the cassette, and each wafer includes a handle oxide that is stripped by the etchant. Each wafer is a silicon-on-insulator wafer or a bonded wafer pair prior to removal of the bulk of the donor wafer thickness, that has been bonded in a preceding step. Each wafer is subjected to a high temperature, gas phase HCl etch or an epitaxial growth step after etchant is applied.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

DETAILED DESCRIPTION

Figure 1:
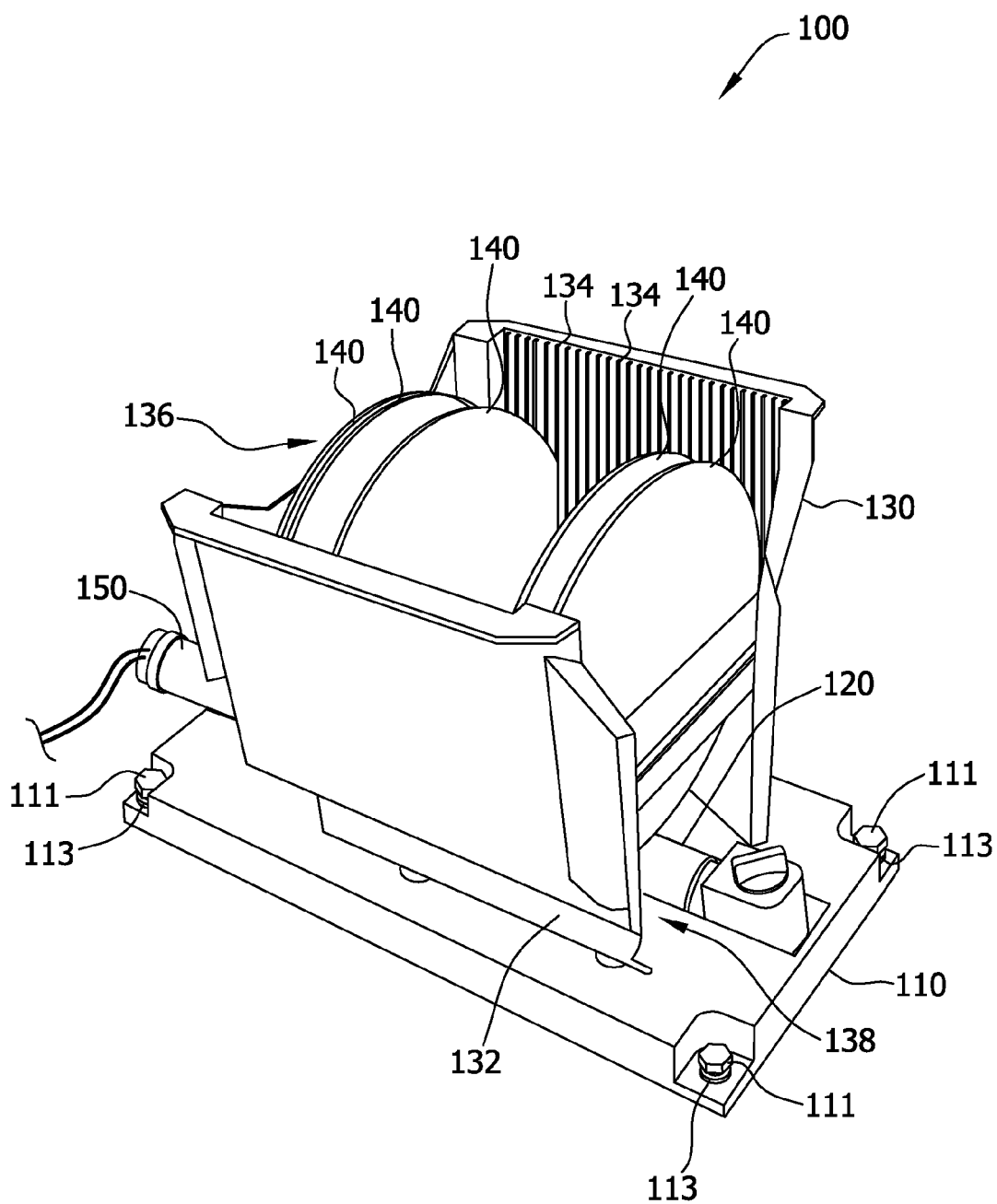
FIG. 1 is a perspective view of a wafer edge etchant application mechanism.
Figure 2:
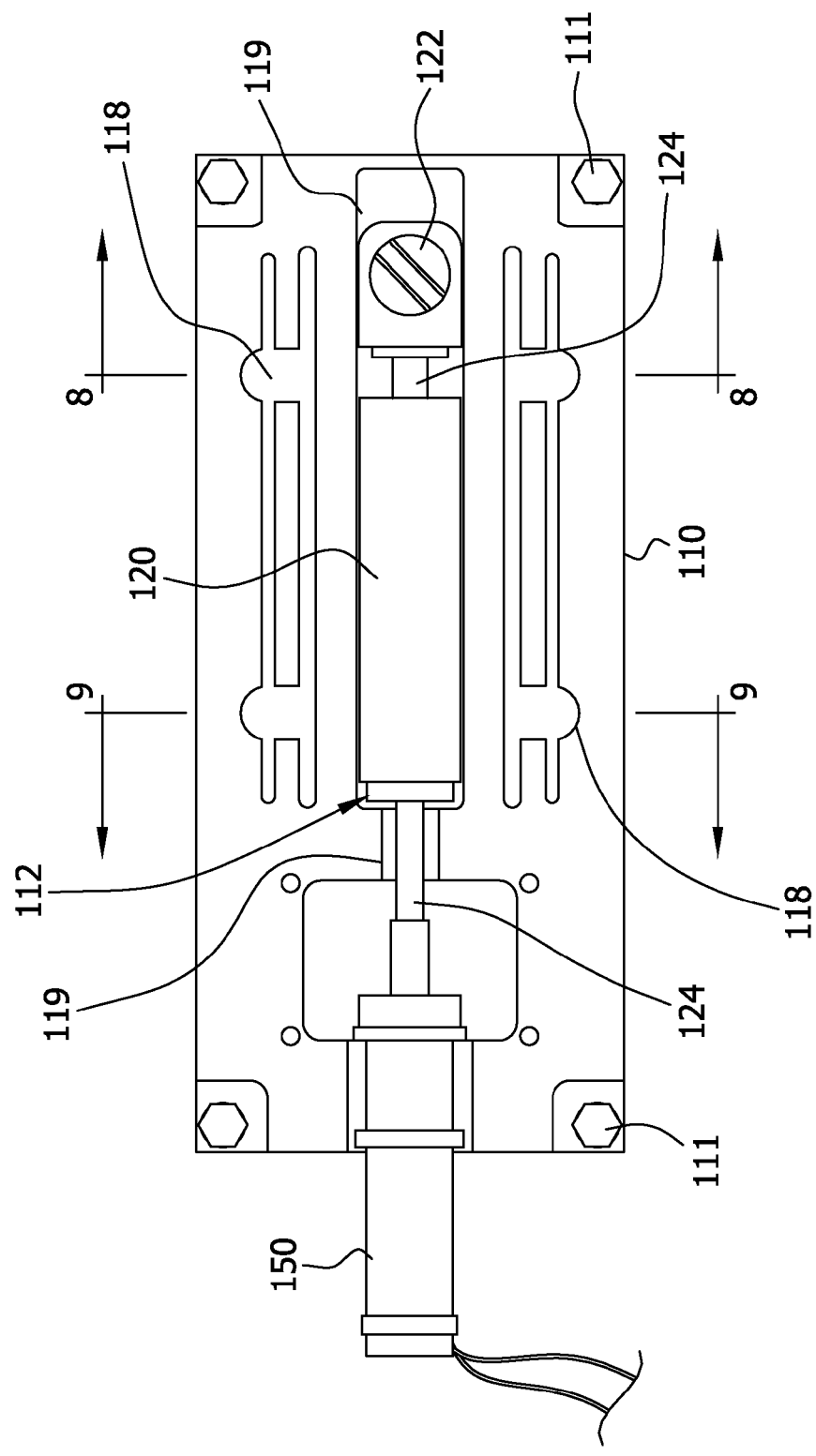
FIG. 2 is a top plan view of the wafer edge etchant application mechanism with a cassette and accompanying wafers removed.
Figure 3:
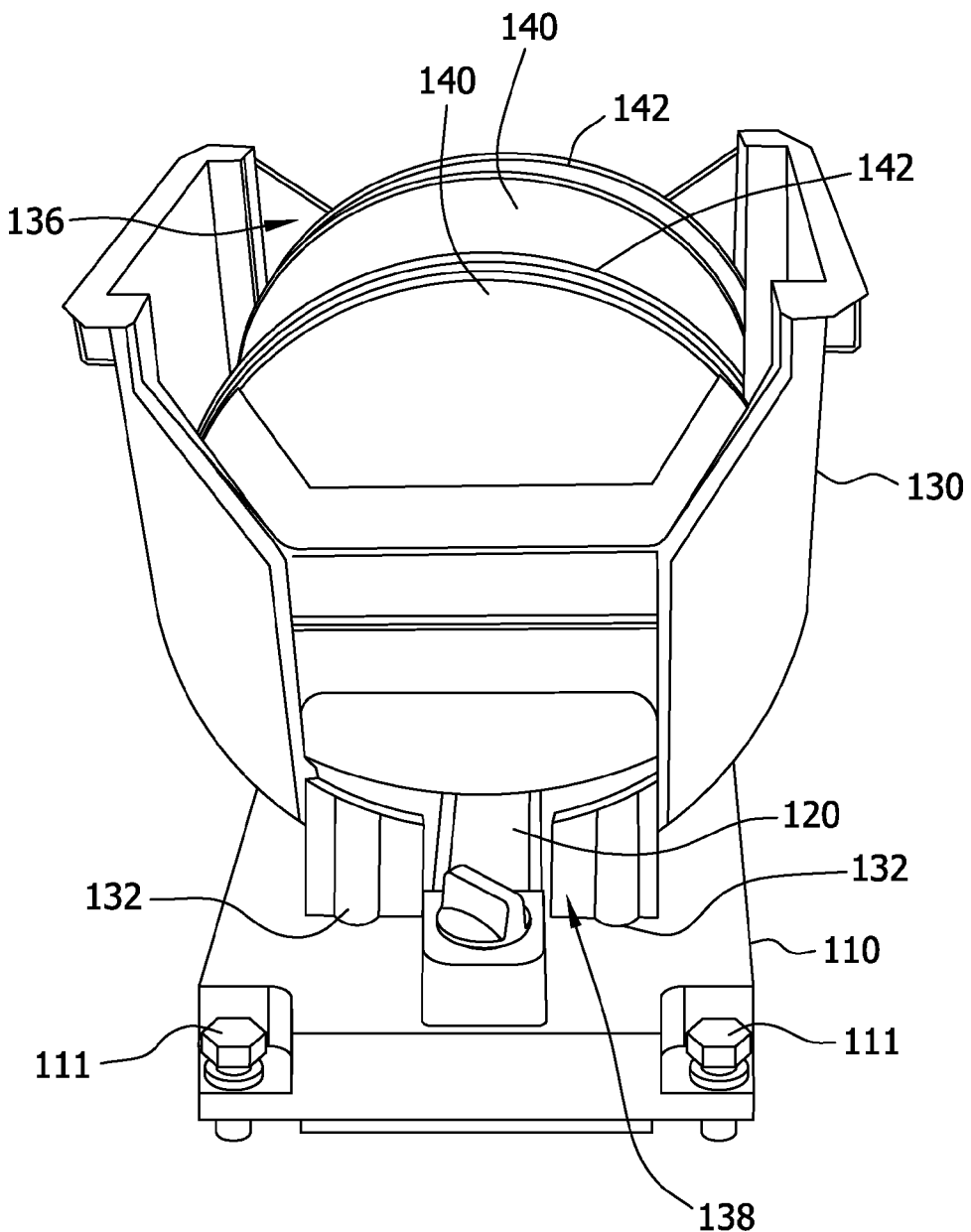
FIG. 3 is a side elevation view of the wafer edge etchant application mechanism.

Referring now to the drawings and in particular to FIGS. 1-3, an etchant mechanism generally referred to as 100 is depicted. The etchant mechanism 100 comprises a sump 110 and a roller 120. A cassette 130 may be included in the etchant mechanism 100, according to some embodiments. The roller 120 and cassette 130 are constructed of materials that are resistant to damage from the etchant, while not being likely to be a source of contamination themselves. Exemplary materials include: fluorinated polymeric materials such as polytetrafluoroethylene (PTFE) or perfluroalkoxy (PFA).

Figure 7:
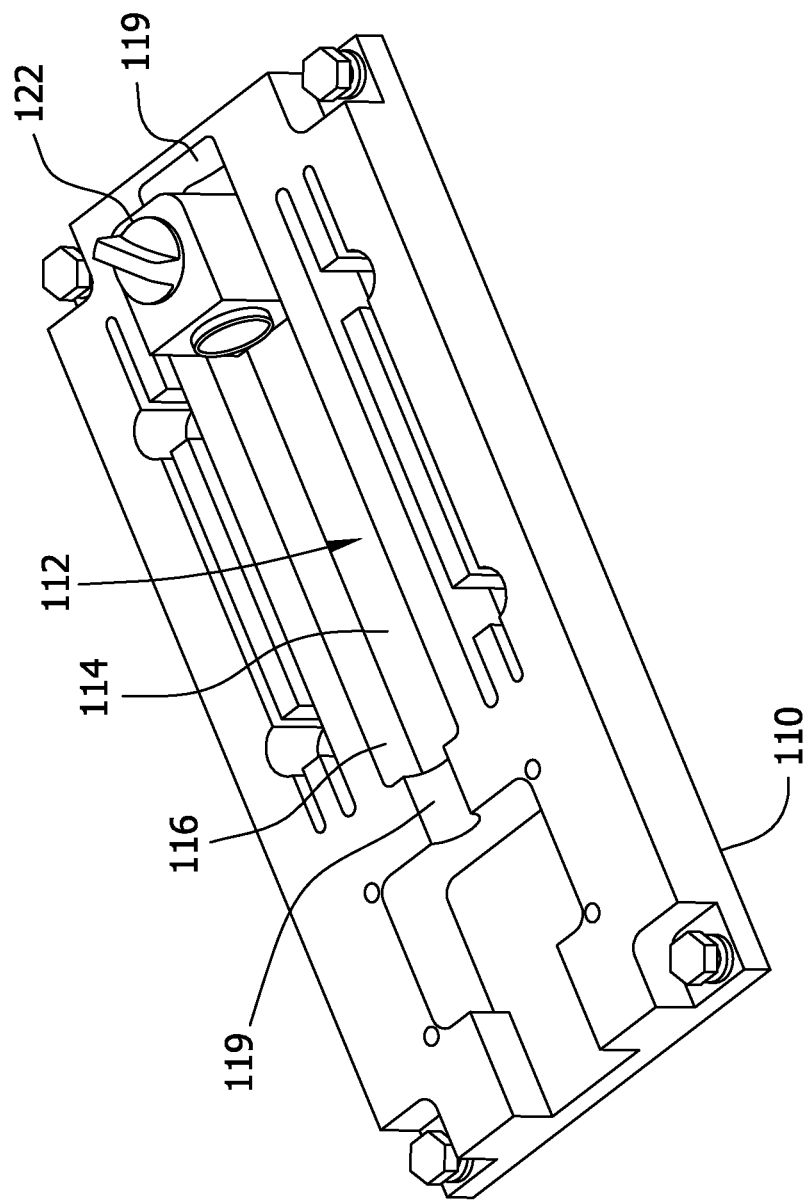
FIG. 7 is a perspective view of a sump included in the wafer edge etchant application mechanism.

The sump 110 (as best seen in FIG. 7) is configured to hold an etchant mixture in a void 112 therein. The void 112 is generally open at its top and has a depth, a length, and a width. The void 112 is defined in the sump 110 by a bottom plate 114 and four side walls 116 perpendicular to the bottom plate. In other embodiments, the sump 110 is constructed from one or more pieces of material that are suitably formed to comprise an enclosure that is capable of containing an amount of liquid etchant. The length, depth and width of the sump 110 are suitably sized to hold a volume of etchant sufficient to etch a plurality of wafers 140. The sump 110 can contain a variety of indentations 118 formed therein for receiving corresponding protrusions formed in a bottom surface of the cassette.

In some embodiments, a fluid connection mechanism 122 may be formed or inserted into a portion of the sump 110 or roller 120. The fluid connection mechanism 122 may be used to transport etchant into the sump 110. An additional fluid connection mechanism (not shown) may also be used to withdraw etchant from the sump 110. The withdrawn etchant may be discarded, or in some embodiments filtered or otherwise processed for reuse.

Figure 4:
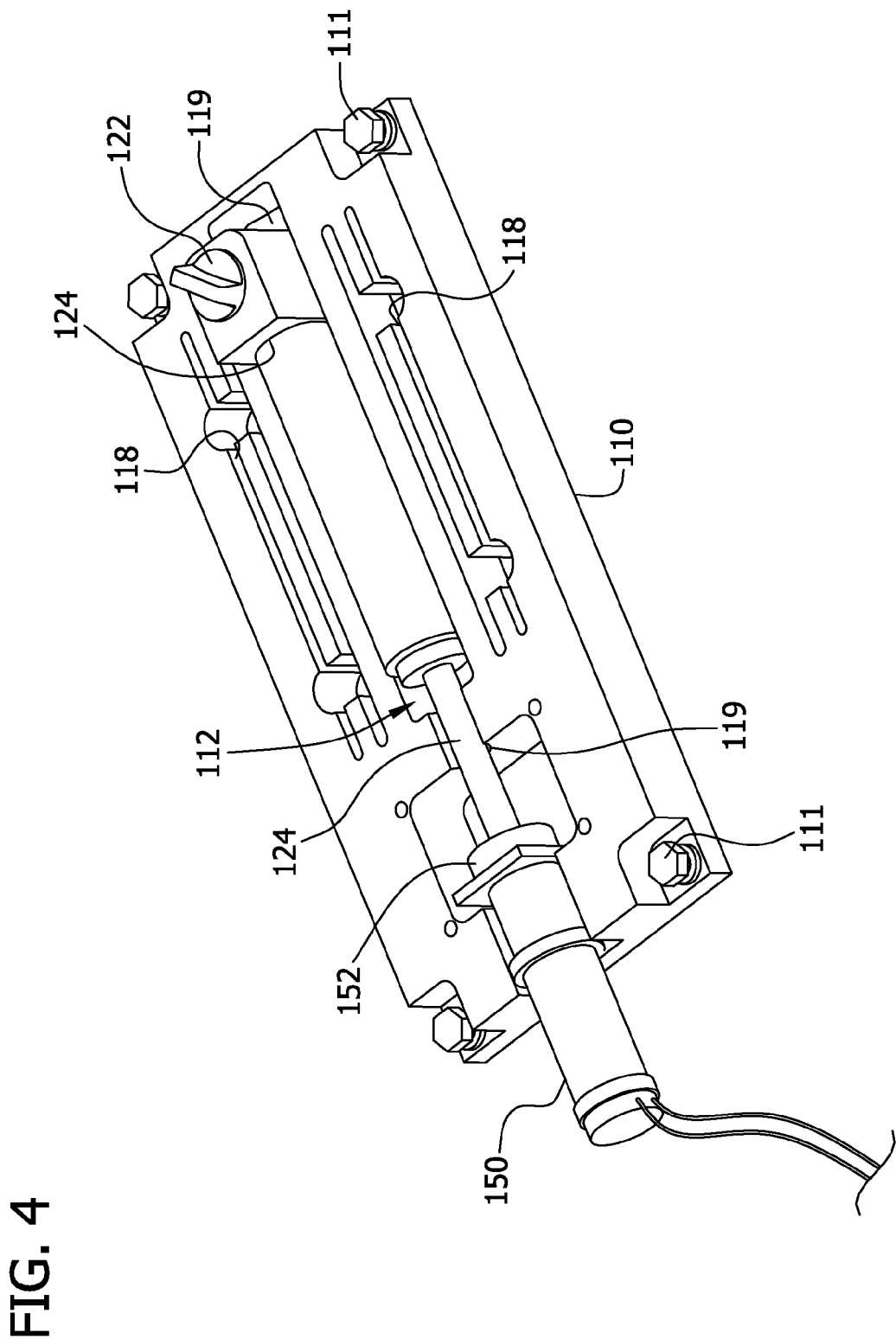
FIG. 4 is a perspective view of the sump, roller, and drive source in an assembled configuration.

At longitudinally opposite ends of the sump, a notch 119 is formed therein to receive the roller (as best seen in FIGS. 2, 4, and 7). According to some embodiments, the notch 119 is configured to receive the outer housing of a roller bearing or other bushing and constrain it from movement, whether longitudinal, lateral, or rotational. Longitudinally opposite ends 124 of the roller are received within the roller bearing or bushing. The roller bearing or bushing serves to restrain lateral and longitudinal movement by the roller 120, while still permitting the roller to rotate about its longitudinal axis.

The sump includes openings 113 formed therein for insertion of leveling legs 111 to level the sump 110 in relation to an underlying surface. The leveling legs 111 may be of any suitable type and the corresponding openings 113 may be sized and positioned based on the dimensions of the leveling legs. Furthermore, the number and location of leveling legs 111 utilized in leveling the sump 110 may be varied based on a number of factors. Although not shown, additional fasteners may be utilized to secure the sump 110 to the underlying surface, or the leveling legs 111 may secure the sump to the underlying surface.

According to some embodiments, the etchant contained in the void 112 of the sump 110 is hydrofluoric acid or a mixture of hydrofluoric acid and acetic acid. In some embodiments, the etchant is a solution of hydrofluoric acid diluted in deionized water. A surfactant or viscosity modifier (e.g., acetic acid) may be added thereto to adjust the rate and radial extent to which the etchant etches the oxide from the wafers 140.

Generally, the acidic etchant is in the form of an aqueous solution comprising a source of hydrogen ions. The source of the hydrogen ions may be selected from the group comprising hydrofluoric acid, nitric acid, phosphoric acid, acetic acid, sulfuric acid, hydrochloric acid, citric acid, oxalic acid, propionic acid, permanaganic acid, and combinations thereof. The source of hydrogen ions may be present in the etchant at a concentration of at least about 40 wt %. In various embodiments, the acidic etchant comprises essentially water and the source of hydrogen ions. In various other embodiments, the acidic etchant comprises one or more additives along with the source of hydrogen ions.

Figure 5:
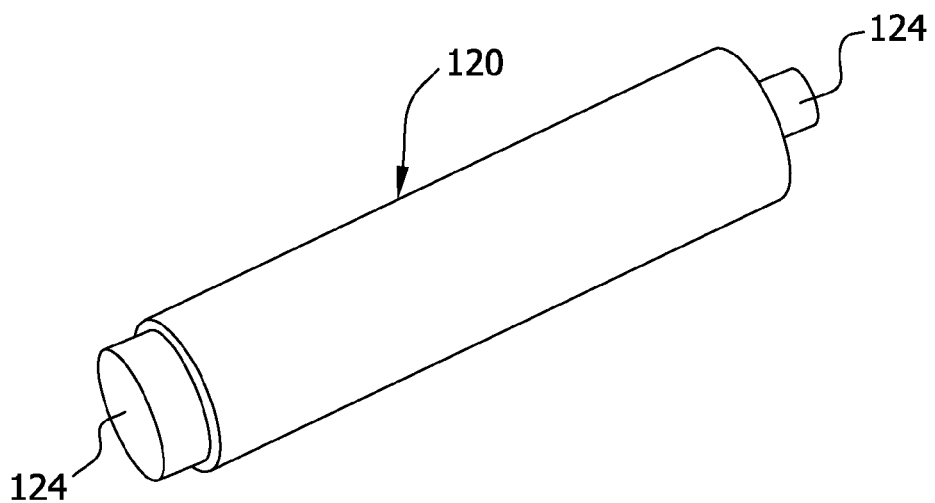
FIG. 5 is a perspective view of a roller included in the wafer edge etchant application mechanism.
Figure 6:
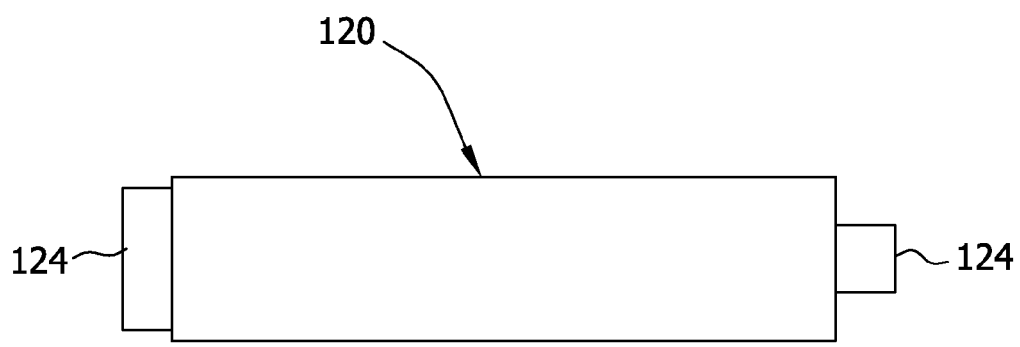
FIG. 6 is side elevation view of the roller depicted in FIG. 4.

Turning now to the roller 120 (best seen in FIGS. 5 and 6), it is generally cylindrical and elongate in shape and is configured to rotate about its longitudinal axis. The length (i.e., depth) of the roller 120 generally exceeds its overall diameter, according to one embodiment. The roller 120 has an outer diameter and a length defined by longitudinally opposite ends 124 of the roller. The longitudinally opposite ends 124 of the roller 120 are configured to be received into the roller bearings or bushings described above.

One or both of the longitudinally opposite ends 124 of the roller 120 are configured for attachment to a drive source 150 by a coupling mechanism 152 (e.g., gears, sprockets, chains, pulleys, belts, shafts, etc.). The coupling mechanism 152 permits the transmission of rotational energy from the drive source to the roller. The drive source 150 is then operable to rotate the roller 120 about its longitudinal axis. In some embodiments, the drive source 150 may be a motor or other similar device capable of generating rotational energy.

In some embodiments, the roller 120 can be comprised of a single piece of material. The material is configured to absorb etchant when the roller 120 comes into contact therewith, and subsequently transfer at least a portion of the retained etchant to a circumferential edge 142 of the wafer 140 that comes into contact with the roller. The circumferential edge 142 includes the surface of the wafer 140 up to 10 mm from the edge (i.e., the terrace region and handle oxide deposited thereon). In some embodiments, the roller 120 may be constructed out of materials such as fluorinated polymeric materials such as polytetrafluoroethylene (PTFE) or perfluroalkoxy (PFA).

While the roller 120 may be comprised of a single piece of material, the physical characteristics of the material may vary. For example, an outer surface of the roller 120 can mechanically altered to increase the amount of etchant which can be absorbed into the outer surface. For example, voids may be formed in the outer surface of the roller 120. In other embodiments, the outer surface of the roller 120 is mechanically altered to resemble bristles of a brush.

Preferably, the roller 120 is constructed of a material that is flexible in composition and more compliant than the wafers in order to reduce the likelihood of mechanical damage to the wafers resulting from contact with the roller. However, the roller is composed of a material that has a sufficient surface roughness so that upon rotation of the roller, the wafers in contact therewith rotate as well.

In this embodiment, the roller 120 is comprised of a cylindrical member and an outer cover surrounding the cylindrical member. Longitudinally opposite ends 124 of the cylindrical member are received in the roller bearings or bushings connected to the sump. Like the embodiment described above, the roller 120 and outer cover are constructed out of materials such as fluorinated polymeric materials such as PTFE or PFA.

In some embodiments, the outer cover is constructed out of a material that is capable of absorbing etchant and retaining it therein and then transferring it to a portion of the wafer that comes into contact with the outer surface. For example, the outer cover can be constructed out of a material that has a sponge-like structure with voids formed therein to retain etchant before dispersing at least some of it on the edge 142 of the wafer 140 that it comes in contact with. Furthermore, the outer cover may be similar in physical construction to a brush, with a substrate and bristles attached therein.

The outer cover may include elastic elements disposed therein to secure the outer cover to an outer surface of the cylindrical member. In other embodiments, different fastening systems can be utilized to secure the outer cover to the cylindrical member (e.g., hook and loop fasteners or adhesives). Accordingly, the outer cover and cylindrical member are securely fastened together to ensure that the outer cover substantially rotates in unison with the cylindrical member when the cylindrical member is rotated (i.e., the outer cover does not slip when the cylindrical member is rotated).

The cassette 130, as seen in FIGS. 1 and 3, and accompanying wafers 140 are placed over the roller 120 and on top of the sump 110, with a portion of the roller coming into contact with the wafers. Protrusions 132 formed in a portion of a bottom surface of the cassette 130 mate with corresponding indentations 118 in the sump 110 to position the cassette relative to the sump. The configuration of the protrusions 132 and indentations 118 are provided for illustrative purposes, and it should be understood that a variety of configurations may utilized according to the embodiments.

The cassette 130 has a plurality of slots 134 (shown in FIG. 1) formed therein for receiving the wafers 140. The slots 134 prevent the wafers 140 from coming into contact with each other and restrain the lateral movement of the wafers. The cassette 130 and the plurality of slots 134 permit the wafers placed therein to rotate about a longitudinal axis of the wafers. The cassette 130, plurality of slots 134, protrusions 132, and indentations 118 are configured such that the longitudinal axis of the wafers 140 when positioned in the cassette is parallel to the longitudinal axis of the roller 120.

According to some embodiments, the wafers 140 have a handle oxide and are silicon-on-insulator wafers or bonded wafer pairs prior to removal of the bulk of the donor wafer thickness, which were bonded in a previous step. The cassette 130 is generally open at its top 136 to permit wafers 140 to be placed therein and subsequently removed. The cassette has a void formed along its longitudinal axis along a bottom portion 138 to permit the circumferential edge 142 of the wafers 140 to selectively come into contact with the roller 120.

When the cassette 130 and wafers 140 are placed atop the sump 110, the wafers are restrained from coming into direct contact with the volume of etchant contained in the void 112 in the sump 110 by the roller 120. The roller 120, in some embodiments, acts to slightly displace the wafers 140 out of their slots 134 in the cassette 130 in the direction of the top 136 of the cassette when the cassette is placed on top of the sump 110, thus decreasing the amount of rotational force required to rotate the wafers. In one embodiment the portions of the cassette 130 which come into contact with the wafers 140 are coated with a low-friction coating, thus reducing the co-efficient of friction for the coated surfaces.

In operation, a portion of the roller 120 is immersed in the etchant contained in the void 112 in the sump 100. As the roller 120 rotates about its longitudinal axis, different portions along a circumference of the roller 120 come into contact with the etchant retained in the void 112 in the sump 110. During one revolution of the roller 120, a fixed point thereon will alternately come into and out of contact with the etchant.

When the roller 120 is rotated, the wafers 140 in contact with the roller rotate as well. The composition of the roller 120, or in some embodiments the outer cover, has a co-efficient of friction sufficient to transmit rotational energy the circumferential edge 142 of the wafer 140. The etchant is transferred to the outer surface of the roller 120 as it passes through the etchant contained in the void 112 in the sump 100 as the roller rotates. The roller 120 then transfers the etchant to the circumferential edge 142 of wafer 140. The rotational velocity of the roller 120 may be altered to control the rate at which etchant is applied to the circumferential edge 142 of the wafer 140, and consequently control the rate and radial extent of etching of the oxide from the donor wafer. Typical rotational velocities of the roller are 2 to 70 revolutions per minute.

After being transferred to the circumferential edge 142 of the wafer 140, the etchant acts upon the silicon oxide in the terrace region of the wafer 140 and removes it therefrom, thus leaving the terrace region free from silicon oxide. The chemical reaction describing the interaction of the silicon oxide is represented by:

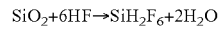

$$SiO_2 + 6HF \rightarrow SiH_2F_6 + 2H_2O$$

The rate of etching, the angular velocity of the roller 120, and the time required to etch the edges 142 of the wafers 140 may each be modified to affect the rate of removal of oxide from the handle. For example, the rate of etching can be slowed by diluting the etchant in de-ionized water. Etchant can be prevented from dripping down either surface of the wafer 140 (beyond the edge 142 where it is brought into contact with the wafer) by adjusting the angular velocity of the rollers 120 or increasing the viscosity of the etchant. For example, the addition of acetic acid to the etchant increases its viscosity without disrupting the chemical reaction of the etching process. The increased viscosity of the etchant prevents it from dripping down the surface of the wafer 140, as well as increasing the ability of the etchant to adhere to the roller 120 during rotation when the roller is not in contact with the edge 142 of the wafer. Furthermore, the viscosity of the etchant can be controlled to affect how much of the edge 142 is contacted by the etchant as increasing the viscosity of the etchant decreases the size of the portion of the edge 142 that is contacted by the etchant.

The embodiments described above include a roller system for the stripping of handle oxide from a narrow annular region on a surface of a bonded wafer. The etchant mechanism is configured for processing wafers while they are in a cassette. Accordingly, multiple wafers can be simultaneously processed as cassettes are capable of retaining a plurality of wafers therein.

The method uses as a starting material a silicon wafer that has been sliced from a single crystal silicon ingot and further processed, for example, by bonding it to another (i.e., a donor) wafer and performing processes thereon resulting in the formation of a bonded wafer pair or silicon-on-insulator (SOI) wafer. The processes may result in the formation of a handle oxide along a circumferential edge (i.e., a terrace region) of the wafer. The terrace may extend up to 10 mm from a circumferential edge of the wafer.

Failure to remove the handle oxide before further processing (e.g., epi-smoothing or epi-thickening) of the wafer increases the likelihood of top silicon thickness non-uniformity and defects being formed near the circumferential edge of the wafer. For example, during an epi-thickening process, small "islands" of polysilicon can nucleate and grow on the handle oxide, thus producing nodule defects can be deleterious to subsequent end-uses of the wafer. Removal of the handle oxide in the terrace region prior to subsequent processing (e.g., epi-thickening) ensures a clean, uniform surface on which other processes may be conducted.

The removal of the handle oxide is interchangeably referred to as stripping or etching throughout the detailed description above. The etching process can be performed at any step between wafer bonding and before an epi-smoothing or thickening process. However, according to some embodiments the etching process is performed prior to the separation of the bonded wafer pair. The bonded wafer pair may be separated by a cleaving operation. When the etching is performed prior to the separation of the bonded wafer pair, the donor wafer protects what will become the surface of the finished wafer from mechanical contact with the cassette and possible damage from contact with the etchant. Generally, the method embodiments described herein comprise treating an edge portion of a bonded silicon wafer pair by removing silicon oxide from a terrace region along a circumferential edge of the bonded pair. A substantial portion of the donor wafer (i.e., the bulk of the donor wafer) is then separated from the bonded wafer after the etchant is applied to the edge portion of the bonded wafer pair. The substantial portion of the donor wafer may be separated from the bonded wafer pair by a cleaving operation.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description and shown in the accompanying drawing[s] shall be interpreted as illustrative and not in a limiting sense.

What is claimed is:

1. A wafer edge etchant application system for applying etchant to edges of a plurality of wafers, the system comprising:
   a sump configured for holding the etchant;
   a roller having an outer surface in fluid communication with the sump, the roller configured to have etchant thereon, the wafers are restrained from coming into direct contact with the etchant in the sump by the roller; and
   a wafer cassette configured to retain wafers positioned therein so that edges of the wafers are in contact with the roller, the cassette permitting axial rotation of the wafers about an axis.

2. The system of claim 1 wherein at least some of the wafers have a handle oxide in a terrace region, the system configured to strip the handle oxide from the terrace region to inhibit nodule growth in the terrace region.

3. The system of claim 1 wherein at least a portion of the roller is disposed in the sump.

4. The system of claim 1 wherein the roller has a longitudinal axis and wherein the roller is operable to rotate about its longitudinal axis.

5. The system of claim 3 wherein the roller is configured to retain at least a portion of the etchant that it comes in contact with in the sump.

6. The system of claim 1 wherein the wafer cassette is configured to hold a plurality of wafers positioned therein.

7. The system of claim 1 wherein the wafer cassette is configured to permit axial rotation of the wafers positioned therein about an axis perpendicular to a planar surface of the wafers, wherein the axis of the wafers is perpendicular to a longitudinal axis of the roller.

8. The system of claim 6 wherein the wafer cassette is configured to permit contact with a circumferential edge of each wafer along the outer surface of the roller.

9. The system of claim 1 wherein the outer surface of the roller is configured to retain at least some of the etchant it comes in contact with in the sump.

10. The system of claim 9 wherein the outer surface of the roller is mechanically modified to increase the amount of etchant retained by the outer surface.

11. The system of claim 8 further comprising an opening formed in the wafer cassette generally adjacent to the outer surface of the roller.

12. The system of claim 11 wherein the opening formed in the wafer cassette permits contact between the circumferential edge of each wafer with the outer surface of the roller.

13. The system of claim 1 further comprising a cover disposed over at least a portion of the outer surface of the roller.

14. The system of claim 13 wherein the cover is configured to retain at least some of the etchant it comes in contact with in the sump.

15. The system of claim 13 wherein the cover is removable.

* * * * *